United States Patent
Racz

(10) Patent No.: US 10,265,504 B2
(45) Date of Patent: *Apr. 23, 2019

(54) SAFETY NEURAL INJECTION SYSTEM AND RELATED METHODS

(71) Applicant: Custom Medical Applications, Farmers Branch, TX (US)

(72) Inventor: N. Sandor Racz, Coppell, TX (US)

(73) Assignee: Custom Medical Application, Farmers Branch, TX (US)

( * ) Notice: Subject to any disclaimer, the term of this patent is extended or adjusted under 35 U.S.C. 154(b) by 73 days.

This patent is subject to a terminal disclaimer.

(21) Appl. No.: 14/210,887

(22) Filed: Mar. 14, 2014

(65) Prior Publication Data

US 2015/0320972 A1 Nov. 12, 2015

Related U.S. Application Data

(60) Provisional application No. 61/794,823, filed on Mar. 15, 2013.

(51) Int. Cl.
*A61B 5/04* (2006.01)
*A61M 25/01* (2006.01)
(Continued)

(52) U.S. Cl.
CPC ..... *A61M 25/0102* (2013.01); *A61B 5/04001* (2013.01); *A61B 6/481* (2013.01);
(Continued)

(58) Field of Classification Search
CPC ............ A61M 25/0068; A61M 25/007; A61M 25/0097; A61M 25/0102; A61M 5/3293;
(Continued)

(56) References Cited

U.S. PATENT DOCUMENTS

| 2,922,420 A | 1/1960 | Cheng |
| 3,565,074 A | 2/1971 | Foti |

(Continued)

FOREIGN PATENT DOCUMENTS

| JP | 2003507110 | * | 2/2003 | ............... A61B 1/00 |
| JP | 2010523218 A | | 7/2010 | |

(Continued)

OTHER PUBLICATIONS

Heavner et al., Sharp Versus Blunt Needle: A Comparative Study of Penetration of Internal Structures and Bleeding in Dogs; 2003; World Institute of Pain; Pain Practice; 3:3; 226-231.

(Continued)

*Primary Examiner* — Bradley J Osinski
*Assistant Examiner* — James D Ponton
(74) *Attorney, Agent, or Firm* — TraskBritt

(57) ABSTRACT

Disclosed herein are safety neural injection systems and related methods of use comprising a cannula, with or without a side port, and a stylet, defined by a first inside diameter, a first outside diameter, a first length, and an open distal end in fluid communication with the inside and outside of the hollow cannula wherein the medicament is administered with the stylet inserted at least partially within the cannula. In various embodiments, the safety neural injection system comprises a metal ball tip.

19 Claims, 7 Drawing Sheets

(51) Int. Cl.
*A61B 10/02* (2006.01)
*A61B 6/00* (2006.01)
*A61M 25/00* (2006.01)
*A61M 5/158* (2006.01)
*A61B 17/34* (2006.01)
*A61N 1/05* (2006.01)
*A61B 17/00* (2006.01)
*A61B 18/14* (2006.01)
*A61B 18/00* (2006.01)

(52) U.S. Cl.
CPC ...... *A61B 10/0233* (2013.01); *A61B 17/3401* (2013.01); *A61B 17/3478* (2013.01); *A61M 5/158* (2013.01); *A61M 25/0068* (2013.01); *A61B 18/1477* (2013.01); *A61B 2017/00455* (2013.01); *A61B 2017/3456* (2013.01); *A61B 2018/00577* (2013.01); *A61B 2018/1425* (2013.01); *A61M 25/007* (2013.01); *A61M 2005/1585* (2013.01); *A61M 2025/0063* (2013.01); *A61N 1/0551* (2013.01)

(58) Field of Classification Search
CPC .... A61M 5/34; A61M 5/3286; A61M 5/3291; A61M 25/0082; A61B 17/3401; A61B 17/3478; A61B 18/1477
See application file for complete search history.

(56) References Cited

U.S. PATENT DOCUMENTS

| | | | |
|---|---|---|---|
| 3,856,009 A | 12/1974 | Winnie | |
| 4,230,123 A | 10/1980 | Hawkins, Jr. | |
| 4,308,875 A | 1/1982 | Young | |
| 4,317,445 A | 3/1982 | Robinson | |
| 4,629,450 A | 12/1986 | Suzuki | |
| 4,973,313 A | 11/1990 | Katsaros | |
| 4,994,034 A | 2/1991 | Botich | |
| 5,022,422 A * | 6/1991 | di Palma | A61M 39/22 137/15.18 |
| 5,106,376 A | 4/1992 | Mononen | |
| 5,242,410 A | 9/1993 | Melker | |
| 5,250,035 A | 10/1993 | Smith | |
| 5,304,141 A | 4/1994 | Johnson | |
| 5,312,360 A | 5/1994 | Behl | |
| 5,336,191 A | 8/1994 | Davis | |
| 5,466,225 A | 11/1995 | Davis et al. | |
| 5,480,389 A | 1/1996 | McWha | |
| 5,571,091 A | 11/1996 | Davis | |
| 5,573,519 A | 11/1996 | Zohmann | |
| 5,628,734 A | 5/1997 | Hatfalvi | |
| 5,669,882 A | 9/1997 | Pyles | |
| 5,730,749 A | 3/1998 | Battenfield | |
| 5,800,445 A | 9/1998 | Ratcliff | |
| 5,810,788 A | 9/1998 | Racz | |
| 5,817,074 A | 10/1998 | Racz | |
| 5,836,914 A | 11/1998 | Houghton | |
| 5,865,806 A | 2/1999 | Howell | |
| 5,871,470 A | 2/1999 | McWha | |
| 6,139,571 A * | 10/2000 | Fuller | A61F 7/12 604/113 |
| 6,146,380 A | 11/2000 | Racz et al. | |
| 6,245,044 B1 | 6/2001 | Daw et al. | |
| 6,283,950 B1 * | 9/2001 | Appling | A61M 25/0075 600/585 |
| 6,387,163 B1 | 5/2002 | Leong | |
| 6,554,809 B2 * | 4/2003 | Aves | A61B 17/3401 604/272 |
| 6,547,769 B2 | 5/2003 | VanTassel | |
| 6,558,353 B2 | 5/2003 | Zohmann | |
| 6,855,132 B2 | 2/2005 | VanTassel | |
| 6,949,087 B2 | 9/2005 | VanTassel | |
| 2004/0260357 A1 | 12/2004 | Vaughan et al. | |
| 2005/0087755 A1 | 4/2005 | Kim et al. | |
| 2005/0107860 A1 * | 5/2005 | Ignagni | A61B 5/04001 607/116 |
| 2008/0200972 A1 | 8/2008 | Rittman et al. | |
| 2010/0069855 A1 * | 3/2010 | Ross | A61M 25/0009 604/268 |
| 2010/0087755 A1 | 4/2010 | Boezaart | |
| 2010/0249750 A1 | 9/2010 | Racz | |
| 2011/0172542 A1 | 7/2011 | Racz | |
| 2014/0018732 A1 * | 1/2014 | Bagaoisan | A61M 25/0147 604/95.04 |

FOREIGN PATENT DOCUMENTS

| | | | | |
|---|---|---|---|---|
| WO | | 03092802 A1 | 11/2003 | |
| WO | WO 2008122008 A1 * | | 10/2008 | ......... A61B 17/3401 |
| WO | | 0113782 A1 | 3/2011 | |

OTHER PUBLICATIONS

Canadian Office Action dated May 1, 2015, in Application No. 2,846,742.
Office Action dated Mar. 7, 2016, in Korean Application No. 2014-31217.
Office Action dated Jan. 26, 2016, issued in Japanese Application No. 2014-051490.
Extended European Search Report dated May 9, 2014, issued in European Application No. 14160306.8.
Office Action dated Apr. 7, 2015, received in Japanese Application No. 2014-051490 filed Mar. 14, 2014.
Office Action dated Jan. 18, 2016, in Korean Application No. 2014-31217.
Office Action dated Jan. 18, 2016, in Korean Application No. 2015-0028266.

* cited by examiner

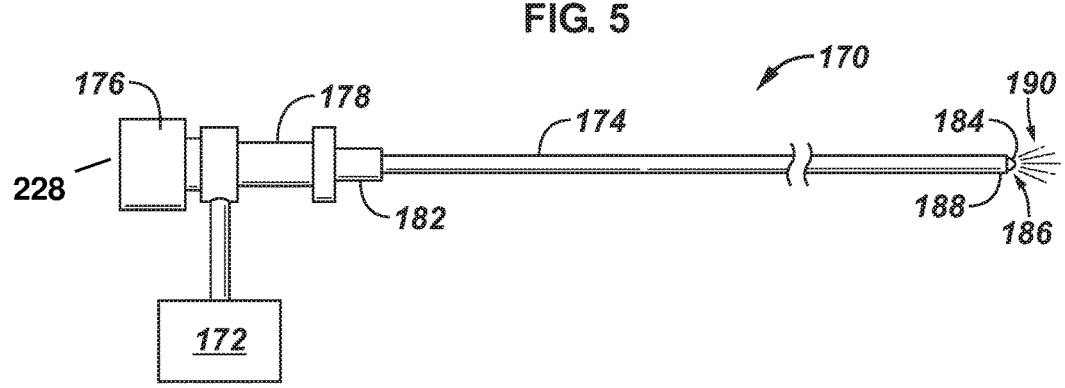
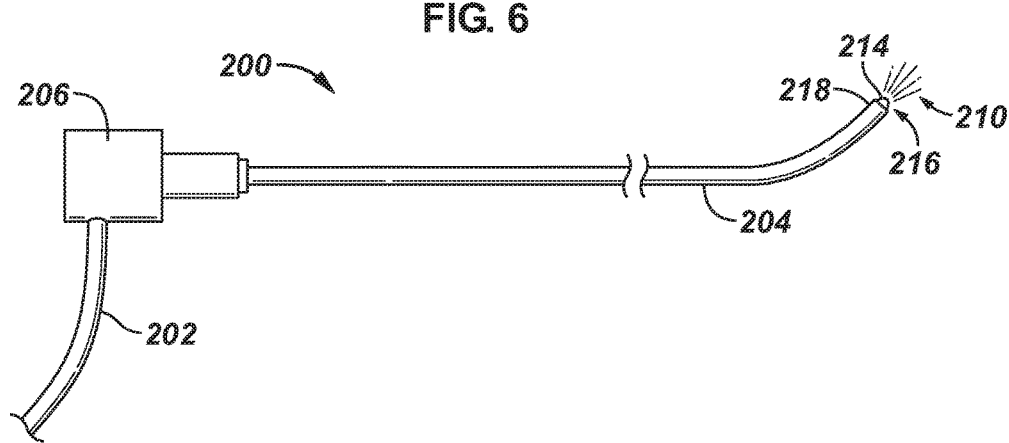

SAFETY NEURAL INJECTION SYSTEM AND RELATED METHODS

FIELD

The present disclosure generally relates to safety neural injection systems and related methods of use.

BACKGROUND

Needles and needle systems are used extensively in a wide variety of procedures which are performed in various fields of medicine, such as cardiology, radiology, urology, interventional pain management, and internal medicine. The use of needles and needle systems in invasive procedures in various medical fields has become routine due, in part, to the ability of needles to pass through most tissues without causing significant destruction to the tissues.

Conventional needles have an orifice or a port at the distal tip of the needle. Distal tips of needles are more liable to clog as the tip of the needle is used for penetration of tissue to access the site of treatment. Additionally, there exists a greater chance of leakage of the agent being delivered, using conventional needles.

Another widely-used type of needle system includes a system that employs a catheter and guide member. Such needle systems generally include a small guide member (e.g., guide wire) which is used to guide a larger hollow catheter to a target area (e.g., a vessel, body cavity, tissue, or organ) within a human or animal body. Such needle systems are efficient for both therapeutic and diagnostic purposes.

It is also desirable to reduce a risk of internal injury from a sharp blade or edge of a traditional injection system or by providing a leading edge that is at least not as sharp, if not smooth, rounded, or flat. The leading edge may also be made of a material that is more yielding if a dense surface is encountered.

SUMMARY

An embodiment of the disclosure comprises a safety neural injection system comprising: an at least partially hollow cannula being defined by a first inside diameter, a first outside diameter, a first length, and a distal end in fluid communication with the inside and outside of the hollow cannula, wherein the hollow cannula comprises a metal ball tip; a side port located coaxially along the hollow cannula in fluid communication between the inside and the outside of the hollow cannula; and a flexible stylet with a shaped tip, wherein the flexible stylet is capable of being releasably locked in a first position within the hollow cannula and extends at least the first length of the hollow cannula; wherein the hollow cannula proximate to the distal end includes a rigid bend so as to facilitate placement of the distal end at a target site, wherein the stylet and the hollow cannula define at least one channel. Another embodiment further comprises an agent selected from the group consisting of a therapeutic agent, a diagnostic agent or a prophylactic agent. In an embodiment, the therapeutic agent is anesthesia. Still another embodiment, further comprises a connector. In yet another embodiment, the safety neural injection system comprises a probe. Various embodiments further comprise a wire, wherein the wire is adapted to be connected about the connector with an instrument. Yet another embodiment further comprises insulation. In an embodiment, the stylet further comprises a side port.

An embodiment of the disclosure includes a method of injecting a medicament at a neuronal tissue comprising the steps of: locating a target site for administration; adjusting the safety neural injection system of claim 1 such that said system is positioned relative to said site; inserting at the target site at least a portion of said safety neural injection system; and administering said agent about said target site. In an embodiment, the agent is selected from the group consisting of a therapeutic agent, a diagnostic agent or a prophylactic agent. In an embodiment, the therapeutic agent is anesthesia.

In further embodiments, the safety neural injection system comprises a biopsy needle.

In various embodiments, a neural map is created of at least a portion of the tissue. In various embodiments, the target site is a site selected from a group consisting of the digestive system, the circulatory system, nervous system, muscular system, skeletal system, respiratory system, urinary system, reproductive system, excretory system, endocrine system, immune system of the human body.

An embodiment of the disclosure comprises a kit comprising the safety neural injection system of claim 1 and an agent to be administered. In an embodiment, the agent is selected from a group consisting of a therapeutic agent, a diagnostic agent or a prophylactic agent.

Figure 1:
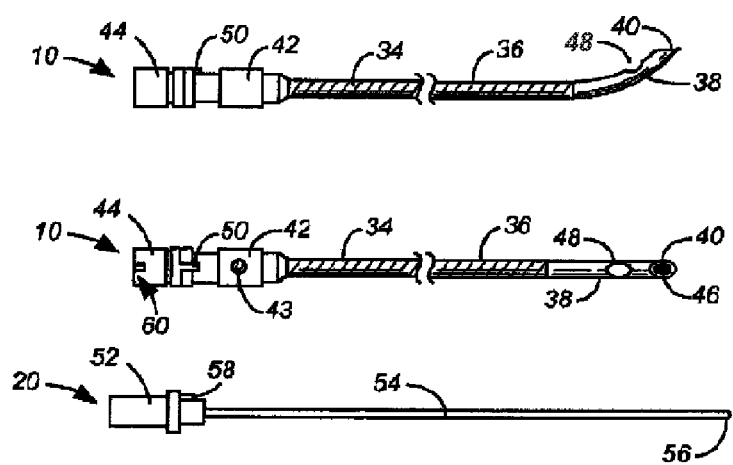
FIG. 1 is an illustration of an embodiment of a safety neural injection system in a disassociated perspective.

LIST OF REFERENCE NUMERALS cannula 10
flexible stylet 20
cannula shaft 34
insulation 36
rigid bent portion 38
distal tip 40
hub 42
index mark 43
stylet mating hub 44
distal opening 46 side port 48
index notch 50
stylet hub 52
shaped tip 56
stylet receiving notch 60
cannula 110
flexible stylet 120
hollow cannula shaft 134
rigid bent portion 138
distal tip 140
hub 142
index mark 143
stylet mating hub 144
distal opening 146
stylet hub 152
stylet receiving notch 160
cannula 170
reservoir 172
cannula shaft 174
stylet mating hub 176
stylet hub 178
second stylet hub 182
mating stylet 184
distal opening 186
distal tip 188
spray marks 190
cannula 200
hollow cannula shaft 204
stylet mating hub 206
second stylet hub 212
mating stylet 214
distal opening 216
distal tip 218
biopsy needle portion 226
connector 228
ball 220
external wire 222
internal wire 224

DETAILED DESCRIPTION

A. Introduction

The present disclosure relates generally to an injection system comprising a hollow cannula with an interior bore and with a proximal and distal end, the distal end being inserted into a subject and a flexible stylet with a shaped tip capable of being inserted into the interior bore of the hollow cannula. The disclosure further comprises a gas or fluid reservoir in fluid communication with the hollow cannula. In various embodiments, the cannula comprises a metal ball tip.

In one embodiment of the disclosure, a cannula having a reservoir attached to the cannula hub is provided wherein a gas or a fluidic therapeutic agent would be stored and dispensed into an insertion path along the hollow bore of a cannula having a stylus inserted into the hollow bore via a mating hub. In a second embodiment of the disclosure, the reservoir is attached to hub of a cannula having a hollow bore and having a stylus inserted through the hollow bore of cannula, wherein the stylus is permanently affixed to the cannula hub. In either embodiment, the reservoir is preferably in fluid connection with the cannula hub. In either embodiment, as an alternative to a gas or fluidic therapeutic reservoir, a vacuum source may be contemplated to aid in aspiration of liquid or cellular matter from a subject having the distal end of the cannula inserted into a cavity of the subject.

In the various embodiments of the disclosure, the reservoir may be in fluid connection to the cannula hub such that a fluidic therapeutic such as a liquid medicament may enter the hollow cannula at the desired time, typically after insertion of the distal end of the cannula into a cavity of the subject. The movement may be controlled such as via a plunger of a syringe, manual pressure placed on the reservoir via the hands of a clinician, pressure placed on the reservoir via a hydraulic pumping mechanism or a piston type pumping mechanism. The movement may also be controlled by gravity such as in the case wherein the reservoir is an IV bag containing a medicament suspended above the subject.

Various embodiments comprise a safety injection and treatment systems and related methods with at least one benefit of enhanced injection characteristics, increased operational efficiency, reduced cost per unit, reduced incidence of injury through intraneural or intravascular injection, reduced incidence of injury through pricking or piercing, or the like.

Various embodiments comprise a safety injection system include an at least partially hollow cannula. The cannula is defined by a first inside diameter, a first outside diameter, a first length, a side port located coaxially along the cannula for fluid communication between the inside and the outside of the hollow cannula, and an open distal end. The system also includes a flexible stylet with a shaped tip, wherein the flexible stylet is capable of being releasably locked in a first position within the hollow cannula and extends at least the first length of the hollow cannula. The hollow cannula is proximate to the distal end includes a rigid bend so as to facilitate placement of the distal end near a target region during system administration.

Various embodiments also includes methods and devices that are designed for injection of minute amounts of a fluid therapeutic, diagnostic or a prophylactic agent into tissue or a body wall, for example, an interior body wall. Additionally, the target site is located at sites or organs located in the human digestive system, the circulatory system, nervous system, muscular system, skeletal system, respiratory system, urinary system, reproductive system, excretory system, endocrine system, immune system of the human body is envisioned using the present disclosure. The amount of the agent to be administered according to the disclosure method will vary depending upon the goal to be accomplished, the size and age of the subject, the pharmacokinetics of the injectate, and the like.

Various embodiments are designed for treatment of a target tissue(s) at a target site. In an embodiment, treatment of a tissue may be at least one of probing, ablation, stimulating, or the like. In general, treatments capable with various embodiments can be any treatment common in the art and should not be limited by the present disclosure.

Figure 2:
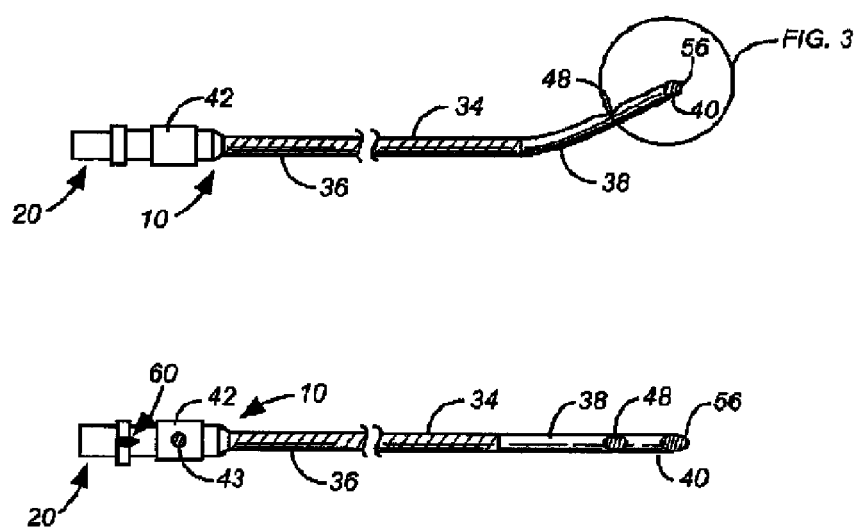
FIG. 2 is an illustration of an embodiment of a safety neural injection system in an associated perspective.

The principles of the present disclosure and their advantages may be understood by referring to FIGS. 1 and 2 of the drawings, like numerals being used for like and corresponding parts of the various drawings.

B. Definitions

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition.

The term "attached," or any conjugation thereof describes and refers the at least partial connection of two items.

The term "medicament(s)" means and refers to all types of fluidic substances that have a beneficial, desired or therapeutic effect. Non-limiting examples of medicaments suitable for use in the disclosure methods include anesthesia, biologically active agents, such as small molecule drugs, proteinaceous substances, polynucleotides or nucleic acids (e.g., heterologous DNA, or RNA) and vectors, liposomes, and the like, containing such nucleic acids or polynucleotides, as well as liquid preparations or formulations thereof.

The term "medical instrument" means and refers to any item, instrument or structure capable of connecting to a catheter, such as, but not limited to a stimulation device, tubing, piping, a medicament delivery system, a meter, a liquid repository (e.g., an I.V. bag), a syringe, or the like.

The term "normal insertion procedure" means and refers to a typical surgical or insertion procedure as disclosed in Heavner et al., "Sharp Versus Blunt Needle: A Comparative Study of Penetration of Internal Structures and Bleeding in Dogs", 2003, World Institute of Pain, Pain Practice, 3:3, 226-231.

The term "stylet" means and refers to a small poniard. Stylets of the present disclosure are capable of being hollow, but such is not required.

Other than in the operating examples, or where otherwise indicated, all numbers expressing quantities of ingredients or reaction conditions used herein are to be understood as modified in all instances by the term "about".

C. Uses

In certain embodiments of the disclosure it is desirable to deliver a therapeutic agent to a subject through the use of a hollow cannula. Any agent that can be injected through a needle can be delivered using the inventive method. Typical agents might include saline solution, drugs, small molecules, pharmaceutical agents, diagnostic agents, biological molecules, proteins, peptides, antibodies, polynucleotides, RNA, DNA, viruses, cells, and combinations thereof. Agents may range in size from small organic molecules to macromolecules such as DNA to intact cells. The agent to be delivered to the injection site may be therapeutic (e.g., chemotherapeutic drug, antibiotic), prophylactic (e.g., vaccine), or diagnostic (e.g., contrast agent for magnetic resonance imaging, labeled metabolite). Therapeutic, prophylactic or diagnostic agents to be delivered may also include biological molecules such as proteins, peptides, polynucleotides, and oligonucleotides. Examples of proteins or peptides include insulin, cytokines, growth factors, erythropoeitin, antibodies, antibody fragments, etc. Polynucleotides may be delivered for gene therapy and anti-sense therapy. In addition to drugs, small molecules, and biological molecules, the disclosure may be used to deliver viruses and cells, such as viruses for gene therapy delivery and cells for stem cell therapy delivery. In general, the therapeutic agent to be delivered will be in a liquid or amorphous form such as an ointment or cream for delivery through a hollow cannula.

In certain other embodiments of the disclosure the hollow cannula and stylet may be used for removal of tissue or liquids from a subject, such as in the use of paracentesis, thoracentesis, imaging via a camera attached or a part of the distal end of the stylet, surgical techniques such as a laser or other cutting instrument attached or a part of the distal end of the stylet, an electrical stimulator at the distal end of the stylet, a dye delivery or radio-isotope delivery system for diagnostic purposes, light delivery from a light emitting mechanism at the distal end of the stylus to visualize tissue or cells and the like.

Various embodiments may include methods of use of a safety neural injection system. An embodiment of a method may include locating a site for treatment in a patient; inserting into a patient at least a portion of a safety neural injection system comprised of an at least partially hollow cannula being defined by a first inside diameter, a first outside diameter, a first length, a side port located coaxially along the hollow cannula for fluid communication between the inside and the outside of the hollow cannula, and an open distal end; a flexible stylet with a shaped tip, wherein the flexible stylet is capable of being releasably locked in a first position within the hollow cannula and extends at least the first length of the hollow cannula; wherein the hollow cannula proximate to the distal end includes a rigid bend so as to facilitate placement of the distal end at the treatment site, maneuvering the distal end of the safety neural injection system inside a patient proximate to the site; and treating the patient.

Further embodiments of a method may include stimulating a tissue. Further embodiments of a method may include ablating at least a portion of the tissue about a site. Other embodiments comprise probing a tissue. And yet further embodiments of a method may include preparing a patient for administering a medicament.

In an embodiment of an administration of a block, such as a nerve block, the method may comprise preparing the patient. In an embodiment, preparing the patient may comprise placing a patient in a supine position or extended position, without a pillow, with the patient's head in a neutral position.

In an embodiment of administration of a medicament, while standing on side of the body that is to be blocked, the physician tactilely locates the cricoid cartilage. In such an embodiment, the neural injection system may be inserted in a position approximately one finger breadth below the cricoid cartilage, between the carotid sheath and the trachea on the side to be blocked, while aiming slightly medially until bony contact is made with the ventral lateral side of the body of the seventh cervical vertebra. When the neural injection system is in said position, the anesthesia may be injected.

In another embodiment, there may be methods for injecting a medicament into tissue of a subject. The method may include inserting the distal portion of an embodiment into the tissue of the subject and causing a therapeutic amount of medicament to enter multidirectionally from a distal end into the tissue. In various embodiments, a stylet is inserted through the cannula to act as a buffer to protect tissue of the patient. In various embodiments, the tissue is neuronal tissue. However, various embodiments of the present disclosure can be used with any tissue.

In various embodiments, the inserted stylet is left in the cannula and the medicament is injected to the target tissue about or around the inserted stylet. In such embodiments, a channel can be formed in the cannula to allow passage of the medicament. In various other embodiments, an interference fit of the stylet and the cannula is such that the medicament passes about the stylet through the distal opening of the cannula.

D. Medical Instruments

Exemplary, non-limiting embodiments of medical instrument, injection systems, and the like that can be modified according to various teachings include, but are not limited to, U.S. Pat. Nos. 6,949,087; 6,855,132; 6,558,353; 6,547,769; 6,387,163; 6,245,044; 5,871,470; U.S. Pat. No. 5,865,806; 5,836,914; 5,817,074; 5,800,445; 5,730,749; 5,669,882; 5,628,734; 5,573,519; 5,571,091; 5,480,389; 5,466,225; 5,336,191; 5,312,360; 5,304,141; 5,250,035 5,242,410; 5,106,376; 4,994,034; 4,973,313; 4,629,450; 4,317,445; 4,308,875; 4,230,123; 3,856,009; 3,565,074; and, 2,922,420, the contents of which are hereby incorporated by reference as if they were presented herein in their entirety.

A cannula associated with various embodiments may be a cylindrical structure extending from a proximal end to a distal end. The length from the proximate end to the distal end, traveling along the length of the cannula is known as the first length. In various embodiments where a bend in the cannula exists, the first length may be longer than the linear distance from the proximate end to the distal end. In an embodiment, the cannula is of a generally constant circumference. The cannula is capable of being differentiated by an inside diameter and an outside diameter. In an embodiment, an outside diameter is between about 0.0355 to about 0.03600 mm and an inside diameter is between about 0.0230 to about 0.0245 mm. In an alternate embodiment, an outside diameter between about 0.0205 to 0.280 mm and an inside diameter between about 0.0155 to 0.0170 mm. In various embodiments, an inside diameter and an outside diameter are capable of being any desired length and any particular length should not be construed as a limitation on the scope of the appended claims.

In various embodiments, a shaped tip end or distal end of the at least partially hollow cannula may take various shapes. In an embodiment, the distal tip may be the traditional beveled angular plane shape. In another embodiment, the distal tip may be squared with the perpendicular of the lengthwise plane of the cannula. In another embodiment, the distal tip may be a partial bevel, wherein the leading portion of the shaped tip is of a traditional bevel form and the remainder of the tip is formed in a non-beveled shape, such as a stair step. A variety of shapes may be considered for use to achieve the desired results while still possessing an open end.

In various embodiments, a connector may be about the proximal end of the cannula. A connector may be used as an attachment means for attaching the cannula and an optional further medical instrument. The connection or connections at the connector end may be any type of connection common in the art, such, as for example, and not by way of limitation, a luer lock connector, a threaded attachment, an interference fit attachment, a clamp, a system utilizing a dowel, two or more of the aforesaid in combination, or the like.

A flexible stylet of various embodiments may extend through at least a portion of the hollow portion of the cannula. In some embodiments, a stylet may be characterized by an outside diameter and a length extending at least from a proximal end to the distal end, representing the first length. The outside diameter, in various embodiments, is smaller than the first inside diameter of the cannula. In various embodiments, the stylet may be of a length that is longer than the first length. In some embodiments, the stylet comprises a side port is at least partially hollow. In an embodiment, the stylet and the cannula define a passageway for passage of at least one medicament.

In various embodiments, the material of construction may permit the flexible stylet so as to bend within the hollow cannula to conform generally to its internal shape. In some embodiments, the material of construction of the flexible stylet may be of a polymer material. In some embodiments, the material will be made of a biocompatible material. Examples of such embodiments include materials such as polyethylene, polypropylene, and polyfluorocarbons. In some alternative embodiments, the material of construction may be of a metallic material. Examples of embodiments include steel alloys, titanium alloys, and aluminum. In various embodiments, the stylet exhibits elastic deformation in regards to insertion and removal from the cannula.

In various embodiments, the flexible stylet may be capable of being inserted into the cannula so that the distal tip of the stylet may be position within the cannula at any point. In an embodiment, the distal end of the stylet may be positioned so that the distal end of the stylet is equivalent with the distal end of the cannula in relation to the proximate end of the cannula. In an alternate embodiment, the distal end of the stylet may extend past the distal end of the cannula. In an alternate embodiment, the distal end of the cannula may extend past the distal end of the stylet.

In various embodiments, the flexible stylet may possess a shaped distal tip to support not only the "safety" function of providing a smooth, flat, or leading surface versus the potentially sharp or rigid edge of the distal tip of the hollow cannula but also provide the means for the leading tip of the system to be later retracted when the flexible stylet is partially or completely decoupled from the hollow cannula so as to retract the shaped tip of the flexible stylet from its leading position. In some embodiments, the shaped tip may be rounded, similar to a half-dome or a bullet. In some embodiments, the shaped tip may be flat in a manner that is squared with the length of the stylet. In some embodiments, the shaped tip may be a traditional bevel angle. In some embodiments, the shape of the tip will conform approximately to the shape of the distal end of the cannula. In some embodiments, the shaped end of the flexible stylet may be formed in a manner so as to form a flush and flat surface with the distal end of the cannula. In some embodiments, the shaped tip may be edged or pointed such that at least a portion of the distal edge of the stylet is capable of penetrating a tissue that a normal insertion procedure could not penetrate. In some embodiments, the shaped tip of the stylet is a point.

Various embodiments may fixedly connect, releasably connect, or leave unconnected the flexible stylet and the cannula. In another embodiment, the stylet is capable of sliding within the cannula. In another embodiment, the stylet is releasably secured within the cannula by a locking mechanism, such as, but not limited to a luer lock, an interference fit, a snap, screw threads, or the like. In an embodiment of a luer lock system, internal male luer threads are located in or about the stylet adjacent to receive and engage a cannula having female luer threads thereon. In other embodiments, the luer lock is reversed. In another embodiment, the cannula is welded to or otherwise fixedly connected to the cannula.

Further embodiments may comprise a cannula or stylet with multiple ports arranged in any orientation about the shaft. In an embodiment, a stylet may comprise, in application, a side port across a cannula and a side port across the stylet. In various embodiments, the side ports may be positioned such that reasonable alignment of the side ports occurs at a desired position of the stylet within the cannula such that a medicament may pass from across the reasonably aligned side ports.

Various embodiments may include a wire or other means of conveying stimulation to a target tissue. In an embodiment, the wire may extends along the cannula from about the proximal end to about the distal end of the distal tip. In another embodiment, the wire may be integral (attached to) with the cannula. In another embodiment, the wire may extend along the outside of the cannula. In another embodiment, a wire may extend along, through, or is integral with the stylet.

Design considerations that may be implemented with various embodiments include, but are not limited to, designing the wire and connector such that they may be utilized as a "plug and use" type of arrangement. A plug and use arrangement is beneficial because it reduces the complexity of the device and reduces loose wires. In an embodiment, the wire may be formed into the connector such that when the connector is connected to another medical instrument, the wire is able to communicate with the instrument. However, any connection common in the art that would allow the wire to communicate with a medical instrument may be contemplated within various embodiments.

Various embodiments may include insulation at least one form insulation about the cannula, stylet, or wire. As may be appreciated by one of ordinary skill in the art, any material of construction that provides electrical or thermal insulation could be used such as, but not limited to, a plastic, a rubber, a metal, a non-metal, or the like. In some embodiments, the insulation covers the exterior of the hollow cannula along the entire first length. In some embodiments, the insulation covers the exterior of the hollow cannula until it reaches the rigid bend portion of the hollow cannula. In some embodiments, the insulation covers an exterior portion of the hollow cannula in between the hub and the rigid bend portion.

An embodiment of a surgical instrument of the present disclosure can include a surgical instrument comprising a tip end, shaft, side port, connector, wing, and medical instrument. Surgical instrument further comprises a wire extending along an interior surface of shaft and an insulation circumferentially surrounding shaft. Tip end comprises tip edge, point, angle, and shoulder. In an embodiment, the surgical instrument comprises insulation, wire, and a metal ball tip.

Various embodiments may include insulation around the hollow cannula, flexible stylet, or wire that is constructed of a material that permits differentiation between the insulation and the hollow cannula or flexible stylet material during real-time procedural use. Numerous procedures, such as, but not limited to, fluoroscopic guidance procedures, NMR procedures, X-ray procedures, neural mapping, direct viewing procedures, or the like, may be used during a medical procedure to determine the position of a safety neural injection system and the target location. In such embodiments, a practitioner may choose an embodiment with an insulation coating wherein the absorptive or reflective difference between the insulation coating and the uninsulated portion of the safety neural injection system can be differentiated in real-time using the selected real-time viewing system. For example, a particular insulation may absorb the energy from a real-time viewing system and show up as a dark segment whereas the uninsulated portion may reflect the energy and appear to be a bright segment. In such embodiments, the differentiation in reflectivity and absorption may provide a method to determine the exact position of the shaped tip, the distal tip, or the side portal of the safety neural needle in relation to the treatment site, given that the relative distance from the insulation/non-insulation border.

Various embodiments comprise a safety neural injection system comprising an at least partially hollow cannula being defined by a first inside diameter, a first outside diameter, a first length, and an open distal end in fluid communication with the inside and outside of the hollow cannula; a side port located coaxially along the hollow cannula in fluid communication between the inside and the outside of the hollow cannula; and a flexible stylet with a shaped tip, wherein the flexible stylet is capable of being releasably locked in a first position within the hollow cannula and extends at least the first length of the hollow cannula; wherein the hollow cannula proximate to the distal end includes a rigid bend so as to facilitate placement of the distal end at a target site. Further embodiments are characterized by the first position of the shaped tip of the flexible stylet being in a flush position relative to the open distal end of the hollow cannula. Further embodiments comprise a side port. In various further embodiments, the stylet is retractable. Further embodiments comprise a kit comprising the safety neural injection system of as herein described and an agent to be injected.

Further embodiments comprise a method of treatment for an individual in need thereof comprising locating a target site of treatment in the individual; adjusting the safety neural injection system of as described above; such that said system is positioned relative to said individual at said site and orientation; inserting at the target site at least a portion of said safety neural injection system; maneuvering the safety neural injection system inside said individual using the rigid bend proximate to the distal end to facilitate placement of said safety neural injection system at said target site; and treating said individual.

Various further embodiments comprise an injection system comprising means for locating a target site for treatment in an individual in need thereof; means for adjusting the safety neural injection system as herein described; such that said system is positioned relative to said individual at said site and orientation; means for inserting into the individual at least a portion of the safety neural injection system as herein described, wherein the hollow cannula, of the safety neural injection system as herein described, proximate to the distal end includes a rigid bend so as to facilitate placement of the distal end at the target site; means for maneuvering the distal end of the safety neural injection system inside said individual proximate to the site; and means for treating the individual.

Certain embodiments of the disclosure concern a safety neural injection system comprising: an at least partially hollow cannula being defined by a first inside diameter, a first outside diameter, a first length, and an open distal end in fluid communication with the inside and outside of the hollow cannula; a side port located coaxially along the hollow cannula in fluid communication between the inside and the outside of the hollow cannula; and a flexible stylet with a shaped tip, wherein the flexible stylet is capable of being releasably locked in a first position within the hollow cannula and extends at least the first length of the hollow cannula; wherein the hollow cannula proximate to the distal end includes a rigid bend so as to facilitate placement of the distal end at a target site, wherein the stylet and the hollow cannula define at least one channel.

In various embodiments, the cannula may comprise multiple side ports or perforations. Multiple side ports are capable of providing a diffuse release of medicament. In an embodiment, the medicament is anesthesia.

Various embodiments includes a retrofitted neural injection system include an at least partially hollow cannula. The cannula is defined by a first inside diameter, a first outside diameter, a first length, a side port located coaxially along the cannula for fluid communication between the inside and the outside of the hollow cannula, and a sealed distal end. In some embodiments, the system also includes a stylet, wherein the stylet is capable of being releasably locked in a first position within the hollow cannula and extends up to a first length of the hollow cannula. In some embodiments, the hollow cannula proximate to the distal end includes a rigid bend so as to facilitate placement of the distal end adjacent to a target site. A cannula associated with various embodiments may be a cylindrical structure extending from a proximal end to a distal end. The length from the proximate end to the distal end, traveling along the length of the cannula is known as the first length. In various embodiments where a bend in the cannula exists, the first length may be longer than the linear distance from the proximate end to the distal end. In an embodiment, the cannula is of a generally constant circumference. The cannula is capable of being differentiated by an inside diameter and an outside diameter. In an embodiment, an outside diameter is between about 0.0355 to about 0.03600 mm and an inside diameter is between about 0.0230 to about 0.0245 mm. In an alternate embodiment, an outside diameter between about 0.0205 to 0.280 mm and an inside diameter between about 0.0155 to 0.0170 mm. In various embodiments, an inside diameter and an outside diameter are capable of being any desired length and any particular length should not be construed as a limitation on the scope of the appended claims.

In various embodiments, a distal end of the at least partially hollow cannula may take various shapes. In an embodiment, the distal tip may be the traditional beveled angular plane shape. In another embodiment, the distal tip is squared with the perpendicular of the lengthwise plane of the cannula. In another embodiment, the distal tip forms a partial bevel, In an embodiment, the leading portion of the shaped tip is of a traditional bevel form and the remainder of the tip is formed in a non-beveled shape, such as a stair step. Regardless of the shape of the distal end of the cannula, the distal end of the cannula should be capable of being sealed by a material so as to close the original open distal end of the cannula.

In various embodiments, a sealant is applied to provide a hermetic seal at the distal end of the at least partially hollow cannula. The seal may be used to block all fluid flow through the formerly open distal end of the cannula. In various embodiments, the sealant may be applied in a moderate amount so that the cutting and leading action of the distal tip is not encumbered by a buildup of sealant on the distal tip. In various embodiments, the sealant may be applied in a moderate amount so that the side port is not encumbered or blocked. In some embodiments, the sealant is composed of a bio-compatible material, such as a thermosetting polymer like an epoxy resin. Aliphatic polymers such as polyethylene or polypropylene may be applied in a liquid form and cooled to a solid state on the distal end of the hollow cannula or in monomer form and cured on the surface of the hollow cannula so as to provide a thin yet resistant film across the open end of the distal end. Another sealant that may be used would be one comprised of a polyfluorocarbon to increase the "slipperiness" of the leading surface. Other sealant materials that may be used are known to those familiar in the medical arts.

In various embodiments, a connector may be about the proximal end of the cannula. A connector may be used as an attachment means for attaching the cannula and an optional further medical instrument. The connection(s) at the proximal end may be any type of connection common in the art, such as, for example, and not by way of limitation, a luer lock connector, a threaded attachment, an interference fit attachment, a clamp, a system utilizing a dowel, two or more of the aforesaid in combination, or the like.

A stylet of various embodiments may extend through at least a portion of the hollow portion of the cannula. In some embodiments, a stylet may be characterized by an outside diameter and a length extending from a proximal end to the distal end, representing the first length. The outside diameter, in various embodiments, is smaller than the first inside diameter of the cannula. In some embodiments, the stylet comprises a side port. In an embodiment, the stylet is at least partially hollow. In an embodiment, the stylet and the cannula define a passageway for passage of at least one medicament.

A side port in various embodiments may be a port extending from the exterior of the hollow cannula to the interior of the hollow cannula or the flexible stylet. The shape of the side port may vary. In an embodiment, a port may be circular. In another embodiment, a port may be ovular. In another embodiment, a port may be a quadrangular port, such as a rectangle or a square. In another embodiment, the port is triangular. It can be seen by one skilled in the art that the shape of the port may be formed in any shape sufficient to permit fluid aspiration.

In further embodiments the safety neural injection system further comprises one or more of the following, a connector, a wire, insulation, or a probe.

A side port in various embodiments may be further characterized by the associated edge of the port on the cannula or stylet. In an embodiment, a port may have a slightly inwardly beveled edge extending from the exterior surface of the hollow cannula to the interior surface. In an alternate embodiment, a port may have a slightly outwardly beveled edge extending from the interior surface of the hollow cannula to the exterior surface. In an embodiment, the degree of bevel may be used to change the pressure of the medicament as it enters the target tissue, facilitate a change in the degree of spread of the medicament, and allow for a smooth surface as the cannula is inserted to the target tissue.

Various embodiments may include insulation around the hollow cannula, flexible stylet, or wire that is constructed of a material that permits differentiation between the insulation and the hollow cannula or flexible stylet material during real-time procedural use. Numerous procedures, such as, but not limited to, fluoroscopic guidance procedures, NMR procedures, X-ray procedures, direct viewing procedures, or the like, may be used during a medical procedure to determine the position of a retrofitted neural injection system and the target location. In such embodiments, a practitioner may choose an embodiment with an insulation coating wherein the absorptive or reflective difference between the insulation coating and the uninsulated portion of the retrofitted neural injection system can be differentiated in real-time using the selected realtime viewing system. For example, a particular insulation may absorb the energy from a realtime viewing system and show up as a dark segment whereas the uninsulated portion may reflect the energy and appear to be a bright segment. In such embodiments, the differentiation in reflectivity and absorption may provide a method to determine the exact position of the shaped tip, the distal tip, or the side portal of the retrofitted neural needle in relation to the treatment site, given that the relative distance from the insulation/non-insulation border.

Further modifications of embodiments of an injection system with a wire comprise the introduction of a probe about the shaft or wire. Various probes capable of use with embodiments include temperature probes, stimulation probes, cameras, or the like.

In an embodiment, the injection system may have a metal ball tip. In various embodiments, the metal ball tip may be used as probe. In certain embodiments, the metal ball tip may be used for neural mapping. The metal ball tip may be comprised of any metal capable of carrying a signal. Metals include, but are not limited to, titanium, titanium alloys, platinum, stainless steel, cobalt alloys, and zirconium alloys. In an embodiment, a wire may be connected to the metal ball tip. In an embodiment, the wire is capable of carrying electricity. In an embodiment, the metal ball tip is capable of detecting an electric signal. In various embodiments, the injection system may be connected to a device for recording the electrical signals. In an embodiment, the device may allow correlation of the electrical signals and the location of nerves. In various embodiments, a neural map maybe created using the injection system to map anatomy, function, or physiology of a given area. In an embodiment, neural map may be created using, but not limited to, NMR, MRI, or PET.

In certain embodiment of the invention the ball is 0.1, 0.2, 0.3, 0.4, 0.5. 0.6, 0.7, 0.8, 0.9, 1, 2, 3, 4, 5, 6, 7, 8, 9 or 10 mm or greater. In certain embodiments, the ball has an outward facing side comprised of any material capable of transmitting an electric signal, a chemical signal or an electromagnetic signal abutting the extreme distal end of the cannula and wherein the maximum perpendicular diameter in reference to a proximal to distal axis of the cannula extends from the distal end of the cannula. In other embodiments, the ball is at the distal end of the cannula. In such embodiments, the cannula has an inner diameter with an inward facing wall. Further, the maximum perpendicular diameter of the ball abuts the inward facing wall of the cannula. In such embodiments the ball has an outward facing surface abutting the inward facing wall of the cannula. Still further, in some embodiments, the ball has an outward facing surface abutting the inward facing wall of the cannula at a location proximal to the distal end of the cannula. In such embodiments the distance from the center of the ball to the distal end of the cannula may be 0.1, 0.2, 0.3, 0.4, 0.5. 0.6, 0.7, 0.8, 0.9, 1, 2, 3, 4, 5, 6, 7, 8, 9 or 10 mm or greater.

In the aforementioned embodiments of the invention concerning the signal transporter operatively connected to or abutting the ball, the signal transporter may be any metal capable of transmitting an electrical signal. In other embodiments, the signal transporter may be a fiber optic transmitter. In further embodiments, the signal transporter may be a chemical or biochemical transporter. In all instances, the transporter is in communication with a signal receiver.

In certain embodiments the signal transporter is within the cannula. In other embodiments, the signal transporter is external to the cannula. In the embodiment wherein the transporter is external to the cannula, the signal transporter may be insulated from the external environment. In other embodiments, the signal transporter may be exposed to the external environment. Likewise in the embodiment wherein the transporter is within the cannula, the signal transporter may be insulated from the internal environment. In other embodiments, the signal transporter may be exposed to the internal environment.

Various embodiments may include methods of manufacture of a retrofitted neural injection system. Various embodiments may include acquiring an injection needle comprising a hollow cannula with an open distal end. In some embodiments, the open distal end is shaped in a beveled form. Then, forming a side port in the hollow cannula proximate to the distal end so as to permit fluid communication between the inside and the outside of the hollow cannula via the newly formed side port. In some embodiments, a plurality of side ports are formed. Formation of a side port in the hollow cannula of the injection needle may be performed using any number of methods known to ones of ordinary skill in the art. Then, sealing the open distal end of the hollow cannula with a bio-compatible sealant so as to eliminate fluid communication between the inside and the outside of the hollow cannula via the distal end. In some embodiments, the bio-compatible sealant may be comprised of a thermosetting material. In some embodiments, the bio-compatible sealant may be comprised of a cured epoxy resin. In some embodiments, the bio-compatible sealant may be comprised of an aliphatic polymer. In some embodiments, the bio-compatible sealant may be comprised of a polyfluorocarbon. Handling, applying, and curing the sealant may be performed using any number of techniques known to one skilled in the art. In some embodiments, the sealant does not hinder the penetrating or leading operation of the distal end of the hollow cannula. Then, in some embodiments, the hollow cannula is forcibly bent so as to impart a rigid bend. Then, in some embodiments, a stylet is included. Then, in some embodiments, a wire is included. Then, in some embodiments, insulation is included.

Further embodiments of a method may include stimulating a tissue. Further embodiments of a method may include ablating at least a portion of the tissue about a site. Other embodiments comprise probing a tissue. And yet further embodiments of a method may include preparing a patient for administering a medicament.

In an embodiment of an administration of a block, such as a nerve block, the method may comprise preparing the patient. In an embodiment, preparing the patient may comprise placing a patient in a supine position or extended position, without a pillow, with the patient's head in a neutral position.

In an embodiment, an occluded nerve block needle comprises a weeping tip portion for microinjection of medicaments into a tissue. In an embodiment, again by way of example, the surgical instrument comprises a nonporous hollow nerve block needle shaft having a connector end adapted to mate with a surgical instrument, a porous distal portion in fluid-tight connection to the nerve block needle shaft, and a closed tip. The porous distal portion of the nerve block needle may be adapted to cause a liquid injectate to weep or ooze therefrom multidirectionally under injection pressure while the distal portion and point of the nerve block needle are inserted into a tissue. In an embodiment, the porous distal portion oozes at a substantially uniform rate.

In embodiments of the safety neural injection system comprising a wire, the wire may be adapted to be connected about the connector with an instrument. In embodiments of the safety neural injection system comprising a connector, the connector may be a plug and use connector.

In embodiments of the disclosure concerning the position of the flexible stylet, in specific embodiments the first position is characterized by the shaped tip of the flexible stylet being in a flush position relative to the open distal end of the hollow cannula. In other specific embodiments, the first position is characterized by the shaped tip of the flexible stylet protruding beyond the first length.

In still further embodiments of the disclosure concerning a stylet, the stylet may itself further comprise a side port. In additional embodiments of the disclosure the stylet is retractable.

Additional embodiments of the disclosure contemplate an agent delivered via the side port attached to the cannula. In such embodiments the agent may be any agent. In particular embodiments, the agent selected from the group consisting of a therapeutic agent, a diagnostic agent or a prophylactic agent. In specific embodiments wherein a therapeutic agent is contemplated the therapeutic agent is anesthesia.

In alternative embodiments of the disclosure, a sideport may not exist in the cannula and the interference fit of the stylet within the cannula is such that medicament is capable of flowing out of the distal end at the target site between the stylet and the cannula.

In still other alternative embodiments of the disclosure, there is no channel and the interference fit of the stylet within the cannula is such that medicament is capable of flowing out of the distal end at the target site between the stylet and the cannula.

Other embodiments of the disclosure concern a method of injecting a medicament at a neuronal tissue comprising the steps of: locating a target site for administration; adjusting the safety neural injection system; such that said system is positioned relative to said site; inserting at the target site at least a portion of said safety neural injection system; maneuvering the safety neural injection system using the rigid bend proximate to the distal end to facilitate placement of said safety neural injection system at said target site; and administering said agent about said target site.

In certain embodiments concerning the aforementioned method, the target is a site selected from a group consisting of the digestive system, the circulatory system, nervous system, muscular system, skeletal system, respiratory system, urinary system, reproductive system, excretory system, endocrine system, immune system of the human body.

In such other embodiments of the disclosure, the agent is may be selected from the group consisting of a therapeutic agent, a diagnostic agent or a prophylactic agent. In particular aspects of the disclosure, wherein the agent is a therapeutic agent, the agent may be anesthesia.

In other embodiments of the disclosure, the safety neural injection system may comprise a biopsy needle. In still other embodiments of the disclosure, the agent is used for stimulating a tissue about the site of the site. In such embodiments, stimulating the tissue may comprise ablating at least a portion of the tissue.

In further aspects of a method of injecting a medicament at a neuronal tissue the method may comprise maneuvering the distal end of the injection system by the use of a real-time imaging device. In such aspects, the implementation of a real-time imaging device may permit a user to determine the exact location of the distal end at the target site.

In further aspects of a method of injecting a medicament at a neuronal tissue, the target site is a site selected from a group consisting of the digestive system, the circulatory system, nervous system, muscular system, skeletal system, respiratory system, urinary system, reproductive system, excretory system, endocrine system, immune system of the human body. In such embodiments, administering an agent may be accomplished with a stylet extending through the cannula. In certain aspects, the stylet can function as a safety measure during insertion of the cannula into the subject. In certain further aspects, the fit between the stylet and the cannula is such that a medicament is capable of passing between the cannula and the stylet.

Other embodiments of the disclosure comprise a kit of the aforementioned safety neural injection system.

Although the present disclosure is described with several embodiments, various changes and modifications may be suggested to one skilled in the art. In particular, the present disclosure is described with reference to certain polymers and materials and methods of processing those materials, but may apply to other types of processing or materials with little alteration and similar results. Furthermore, the present disclosure contemplates several process steps that may be performed in the sequence described or in an alternative sequence without departing from the scope and the spirit of the present disclosure. The present disclosure is intended to encompass such changes and modifications as they fall within the scope and the spirit of the appended claims.

E. Specific Embodiments

FIG. 1 illustrates an embodiment of a safety neural injection system 1 with a cannula 10 (viewed in both top and side perspectives) and a mating flexible stylet 20 in a disassociated manner. The cannula 10 is capable of being characterized as having a first length measured from the proximate end of the stylet mating hub 44 to the distal opening 46 of the distal tip 40. In this embodiment, the cannula 10 has a hollow cannula shaft 34 with a rigid bent portion 38 near the distal end and possesses insulation 36 lining part of the cannula shaft 34. Insulation 36 is capable of use to isolate a radio frequency (RF) portion of the cannula, to isolate an RF wire, and/or the like. However, various embodiments comprise a cannula without insulation.

Nerve block systems are used to inject anesthetic onto or near nerves for temporary control of pain or as a diagnostic tool. Nerve block needles are used to intentionally target specific areas and neural structures for injection. Sharp needles are predominantly used for quick and easy injections. Blunt needles where introduced to safely approach nerve structures without piercing or damaging the nerve.

Curving radiofrequency needles aid in the accurate placement of the needle tip ("Bent tip electrical surgical probe" U.S. Pat. No. 6,146,380, incorporated by reference). The concept of curved needles was adopted for various other standard (non-radiofrequency) nerve block needles.

More particularly, embodiments of the present disclosure generally comprise a surgical instrument comprising an elongated at least partially hollow shaft, generally extending from a proximal end to a distal end; a sharp needle at least partially occluded, closed distal end or tip end; a connector end; and, at least one side port located coaxially along the shaft. In further embodiments, the surgical instrument further comprises a medical instrument, i.e., any item, instrument or structure capable of connecting to a connector, such as, but not limited to a stimulation device, tubing, piping, a medicament delivery system, a meter, a liquid repository (such as an I.V. bag), a syringe, and/or the like connected to the connector end.

An embodiment of the disclosure includes a nerve block system. Further embodiments comprise stimulating the site and/or ablating the site. In further embodiments, the patient is in need of access to a particular tissue.

Various embodiments of the present disclosure further comprise a wire or other means of conveying stimulation to a target tissue. In an embodiment, by way of example, the wire extends along the inside of the interior of the shaft from the connector to the tip. In an alternate embodiment, again by way of example, the wire is integral with the shaft. In an alternate embodiment, again by way of example, the wire extends along the outside of the shaft. It is preferred to have the wire secured to a surface so that the wire is not loose.

However, any connection common in the art that would allow the wire to communicate with a medical instrument is contemplated within the various embodiment of the present disclosure.

Further modifications of embodiments of a surgical instrument with a wire comprise the introduction of insulation about the cannula and/or wire. In general, any method of insulation or type of insulation could be used such as, but not limited to, a plastic, a metal, and/or the like.

Further modifications of embodiments of a surgical instrument with a wire comprise the introduction of a probe about the shaft and/or wire. Various probes capable of use with embodiments of the present disclosure include temperature probes, stimulation probes, cameras, and/or the like.

In various other embodiments, the nerve block needle and/or blunt surgical assemblage is ideally suited for injection into tissue of medicaments containing nucleic acid encoding a therapeutic agent (or cells containing such nucleic acid), For example, the nerve block needle (when attached to an appropriate needle or catheter) or disclosure surgical assemblage can be used to inject medicament(s) into the wall of a beating heart or other internal organ, without substantial loss of the medicament at the surface of the body wall and without substantial damage to tissue at the injection site caused by injectate.

A nerve block is a chemical paralysis of the nerve by a local anesthetic agent injected in the vicinity of the nerve. In one embodiment, the procedure is a stellate ganglion nerve block. When a predetermined amount of blocking agent is correctly injected, the middle cervical ganglion, the intermediate ganglion, the stellate ganglion and the second, third, and fourth thoracic ganglia are anesthetized ("blocked"). Additionally, the superior cervical ganglion is also anesthetized because the nerve fibers that form this ganglion extend through the above-mentioned ganglia. Thus, when a stellate ganglion sympathetic block is correctly executed, the entire cervicothoracic portion of the sympathetic nervous system is blocked. Generally, for short time duration blocks, local anesthetic drugs such as novocaine, pontocaine, xylocaine, metycaime and intracaine, nupercaine and the like are used. For long time duration blocks, alcohol and phenol are generally used.

In various embodiments of procedures for blocks, a physician relies on superficial landmarks (i.e. bones, cartilage, muscles, tendons, and blood vessels which are near the skin surface) to locate the area of insertion of the needle. Deep landmarks (i.e. bones, periosteum, fascial planes, tendons, and blood vessels) that cannot be seen or palpated can only be felt with the tip or distal end of the needle. Thus, the accuracy in identifying these deep landmarks depends greatly on the educated touch of the physician.

Exemplary, non-limiting embodiments of medical instrument, surgical instruments, and/or the like that can be modified according to various teachings of the present disclosure include, but are not limited to, U.S. Pat. Nos. 6,949,087; 6,855,132; 6,558,353; 6,547,769; 6,387,163; 6,245,044; 5,871,470; 5,865,806; 5,836,914; 5,817,074; 5,800,445; 5,730,749; 5,669,882; 5,628,734; 5,573,519; 5,571,091; 5,480,389; 5,466,225; 5,336,191; 5,312,360; 5,304,141; 5,250,035; 5,242,410; 5,106,376; 4,994,034; 4,973,313; 4,629,450; 4,317,445; 4,308,875; 4,230,123; 3,856,009; 3,565,074 and, 2,922,420, the contents of which are hereby incorporated by reference as if they were presented herein in their entirety. In general, any catheter may be used with the various embodiments of the present disclosure.

In various embodiments, a measurement that is capable of differentiating various embodiments of the present disclosure is the measurement from the shoulder of the tip to an edge of a port. In general, embodiments of the present disclosure comprise any shaft wherein the nerve block needle is not adjacent to a shoulder of the tip end. By not being adjacent means that a shoulder of a tip and a port on the shaft are at least separated by some distance. In an embodiment, by way of example, the distance is between about 0.01 mm to about 100.0 mm. In an alternate embodiment, again by way of example, the distance is between about 0.5 mm to about 75.0 mm. In an alternate embodiment, again by way of example, the distance is between about 1.0 mm to about 50.0 mm. In an alternate embodiment, again by way of example, the distance is between about 5.0 mm to about 25 mm. In general, the distance between the shoulder of the tip and the port of the associated shaft can vary as needed for the particular application.

In an embodiment, a side port 48 is located in the rigid bent portion 38 of the hollow cannula shaft 34 proximate to the distal tip 40 and distal opening 46. However, a side port is not present in various other embodiments. At the proximate end of the cannula 10, a hub 42 is endowed with an index mark 43 to visually inform the user of the direction of bend the rigid bent portion 38 is directed toward. Additionally, an index notch 50, located on the stylet mating hub 44, performs a similar function tactilely so as to inform the user of the directional perspective of the rigid bent portion 38. The stylet mating hub 44 also possesses a stylet receiving notch 60 so as to fixedly engage a flexible stylet 20 and directionally fix its position.

In this embodiment, the flexible stylet 20 is comprised of a stylet hub 52 with a stylet lock notch 58 shaped to mate with the stylet receiving notch 60 in a frictional manner, a stylet shaft 54, and a shaped stylet tip 56. The stylet shaft 54 is characterized by having a length of at least the first length associated with the first length of the cannula 10. The stylet shaft is also characterized by a material of construction that permits elastic return even after prolonged engagement within a hollow cannula 10 with a rigid bent portion 38.

FIG. 2 illustrates another embodiment of a safety needle injection system wherein the flexible stylet 20 that extends beyond the first length of the cannula 10 possessing a shaped tip 56 is mated and engaged with a cannula 10 with a side port 48, a distal tip 40, a rigid bent portion 38, and insulation 36.

Figure 3:
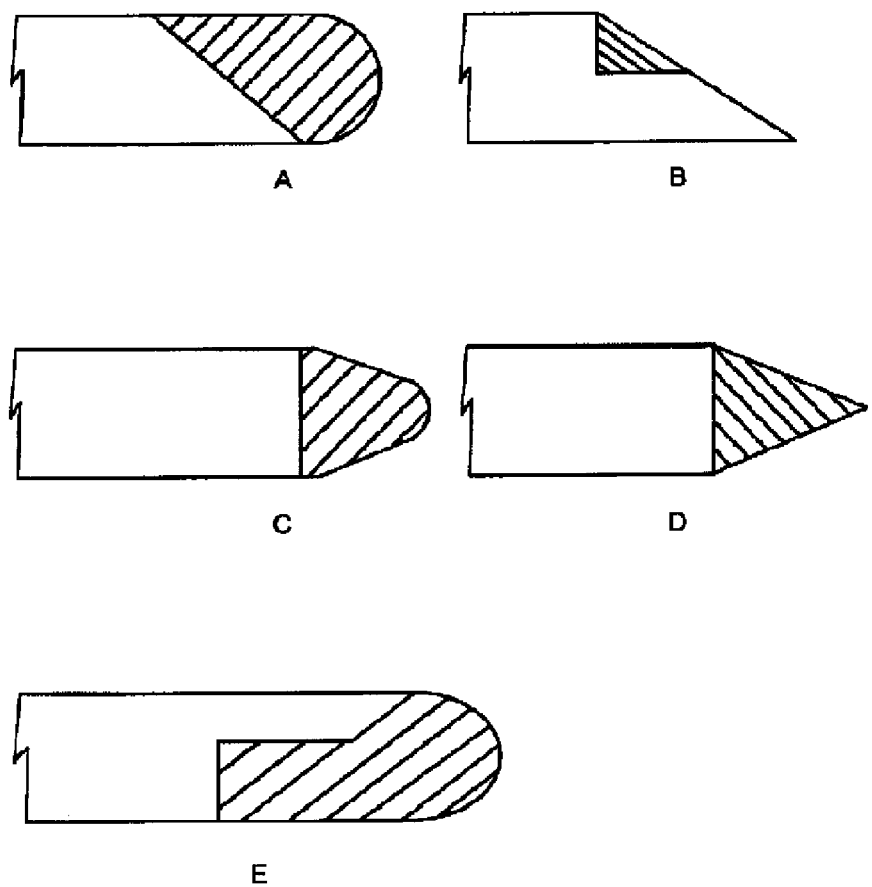
FIGS. 3A-3E are illustrations of embodiments of distal tips of hollow cannulas associated with shaped tips of flexible stylets; and, FIG. 4 is an illustration of an alternate embodiment of a safety neural injection system in a disassociated perspective.

FIGS. 3A-3E illustrates more closely several embodiments of the distal tip 40 of the cannula 10 with the shaped tip 56 of the flexible stylet 20. FIG. 3A shows an example of a shaped tip 56 as a rounded end extending beyond the end of the traditional bevel shape of the distal tip 40. FIG. 3A also inherently demonstrates a flexible stylet 20 that has a stylet shaft 54 that is longer than the first length of the associated cannula 10 because the end of the flexible stylet 20 extends beyond the furthest distal point of the distal tip 40. FIG. 3B shows an example of a partial bevel distal tip 56 at the distal end of a cannula 10 matched with tip of a flexible stylet 20, wherein the shape of the shaped tip 56 corresponds with the angle of the bevel portion of the distal tip 56 and forms a partially flush and flat surface at the open distal end 40. Such a combination of shapes that form a flush, beveled surface might be intended for use to prevent tearing and "grabbing" of the distal tip on parts of the body by the more squared portion of the distal tip 40. FIGS. 3C and 3D show a distal tip 40 in a squared form with flexible stylet shaped tips 56 extending beyond the first length. FIG. 3C gives an example of a rounded point or "pen point" form for shaped tip 56. FIG. 3D gives an example of a sharp leading point for shaped tip 56. FIG. 3E is an illustration of the needle tip disclosed in U.S. Pat. No. 5,810,788, the contents of which are hereby incorporated by reference.

Figure 4:
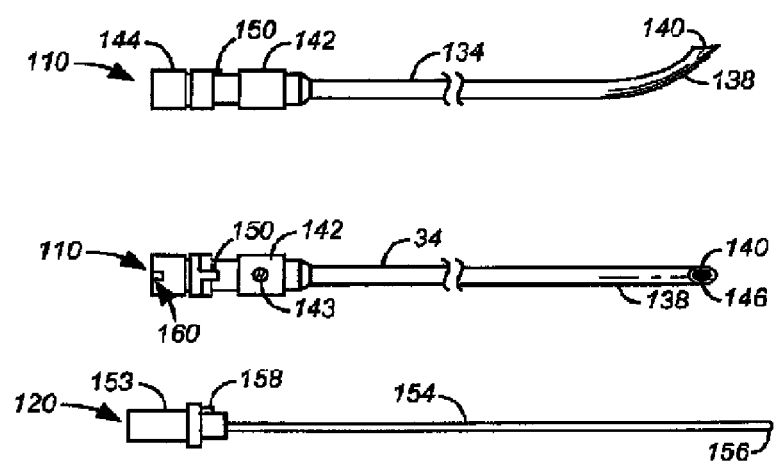

FIG. 4 illustrates an alternate embodiment of a safety neural injection system with a cannula 110 (viewed in both top and side perspectives) and a mating flexible stylet 120 in a disassociated manner. The cannula 110 is capable of being characterized as having a first length measured from the proximate end of the stylet mating hub 144 to the distal opening 146 of the distal tip 140. In this embodiment, the cannula 110 has a hollow cannula shaft 134 with a rigid bent portion 138 near the distal end.

The proximate end of the cannula 110, a hub 142 is endowed with an index mark 143 to visually inform the user of the direction of bend the rigid bent portion 138 is directed toward. Additionally, an index notch 150, located on the stylet mating hub 144, performs a similar function tactilely so as to inform the user of the directional perspective of the rigid bent portion 138. The stylet mating hub 144 also possesses a stylet receiving notch 160 so as to fixedly engage a flexible stylet 120 and directionally fix its position.

In this embodiment, the flexible stylet 120 is comprised of a stylet hub 152 with a stylet lock notch 58 shaped to mate with the stylet receiving notch 160 in a frictional manner, a stylet shaft 154, and a shaped stylet tip 156. The stylet shaft 154 is characterized by having a length of at least the first length associated with the first length of the cannula 110. The stylet shaft is also characterized by a material of construction that permits elastic return even after prolonged engagement within a hollow cannula 110 with a rigid bent portion 138.

Figure 5:
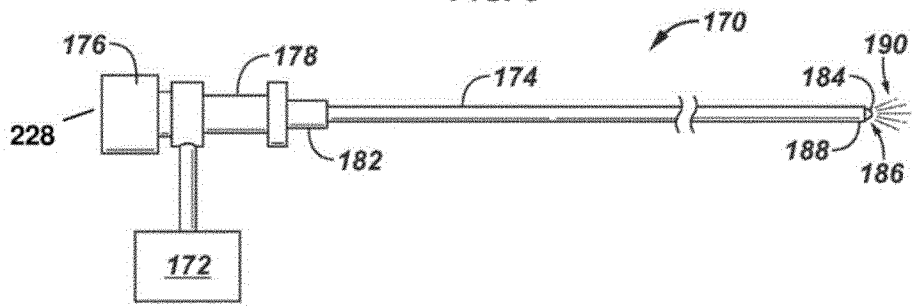
FIG. 5 is an illustration of an embodiment of a neural injection system with a cannula.

FIG. 5 illustrates an alternate embodiment of a neural injection system with a cannula 170 and a mating stylet 184 in an associated manner. The cannula 170 is capable of being characterized as having a first length measured from the proximate end of the stylet mating hub 176 to the distal opening 186 of the distal tip 188. In this embodiment, the cannula 170 has a hollow cannula shaft 174 that is straight and at least semi rigid. A connector 228 is present in this embodiment.

The proximate end of the cannula 170, a hub 178 is connected to a reservoir 172. Additionally, indexing on stylet hub 178 and second stylet hub 182 can be used to tactilely and/or visually inform the user of the location of the stylet within cannula 170.

In this embodiment, stylet 184 and cannula 170 define a fluid passageway wherein a user can inject a medicament as is shown by spray marks 190 out of distal opening 186 without removing stylet 184. Such an embodiment is capable of use when injecting a medicament around neuronal tissue that may be damaged by a cannula without the protection of the stylet. In this embodiment, stylet 184 extends beyond cannula shaft 174 and is capable of providing a buffer for neuronal tissue. In various other embodiments, the stylet extends through the cannula shaft.

Figure 6:
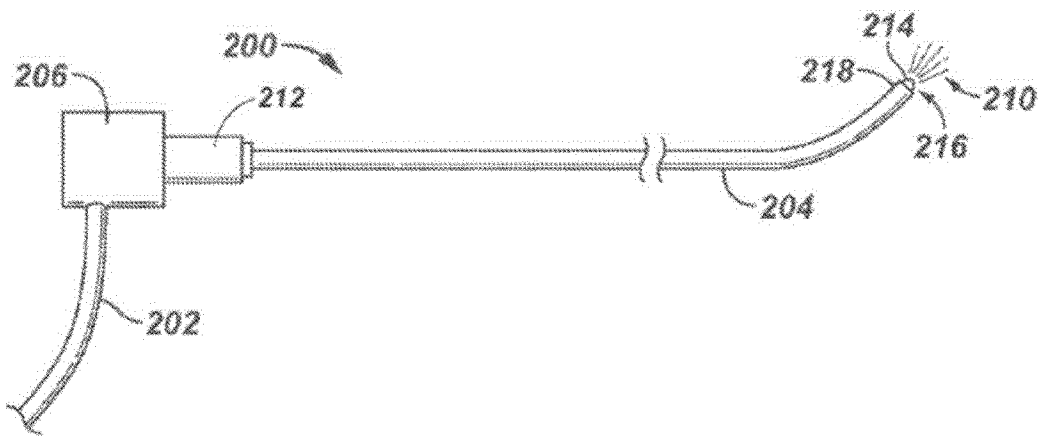
FIG. 6 is an illustration of an alternate embodiment of a neural injection system with an alternate cannula and an alternate mating stylet in an associated manner.

The cannula may be curved or straight. In various embodiments, the distal end of the cannula may be curved. FIG. 6 illustrates an alternate embodiment of a neural injection system with a cannula 200 and a mating stylet 214 in an associated manner. The cannula 200 is capable of being characterized as having a first length measured from the proximate end of the stylet mating hub 206 to the distal opening 216 of the distal tip 218. In this embodiment, the cannula 200 has a hollow cannula shaft 204 that is bent.

The proximate end of the cannula 200, hub 206 is connected to a reservoir line 202 that is capable of supplying a medicament or other fluid, such as a liquid or a gas. Additionally, indexing on stylet hub 206 and second stylet hub 212 can be used to tactilely and/or visually inform the user of the location of the stylet within cannula 200.

In this embodiment, stylet 214 and cannula 200 define a fluid passageway wherein a user can inject a medicament as is shown by spray marks 210 out of distal opening 216 without removing stylet 214. Such an embodiment is capable of use when injecting a medicament around neuronal tissue that may be damaged by a cannula without the protection of the stylet. In this embodiment, stylet 214 extends beyond cannula shaft 204 and is capable of providing a buffer for neuronal tissue.

Figure 7:
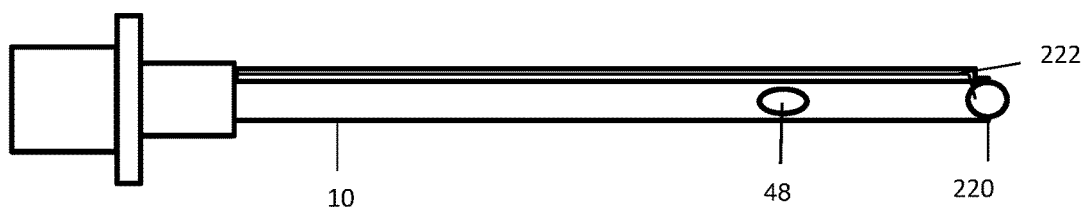
FIG. 7 is an illustration of an embodiment of a neural injection system with a cannula with a ball at the distal tip connected by an external wire which may in turn be connected to a sensor.

FIG. 7 is an embodiment of the present invention comprising the cannula 10 with a side port 48 and with a ball 220 at the distal tip 218. In this embodiment, the ball is connected to an external wire 222 which may in turn be connected to a sensor.

Figure 8:
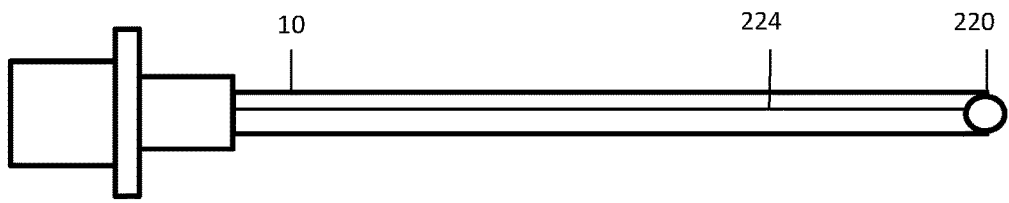
FIG. 8 is an illustration of an embodiment of a neural injection system with a cannula with a ball at the distal tip connected to an internal wire which may in turn be connected to a sensor.

FIG. 8 is an embodiment of the present invention comprising the cannula 10 with a ball 220 at the distal tip 218. In this embodiment, the ball is connected to an internal wire 224 which may in turn be connected to a sensor.

Figure 9:
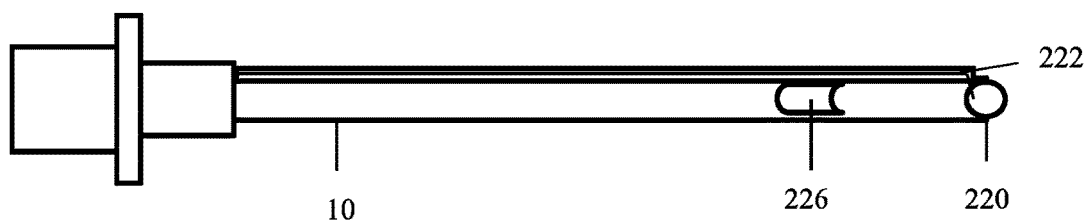
FIG. 9 is an illustration of an embodiment of a neural injection system with a cannula a biopsy needle portion and with a ball at the distal tip connected by an external wire which may in turn be connected to a sensor.
Figure 1:
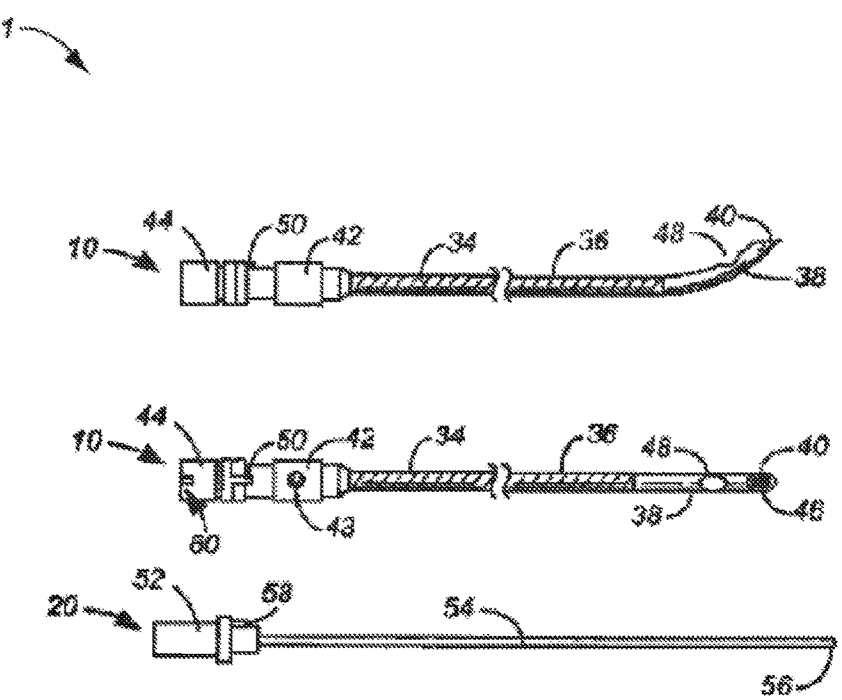
Figure 4:
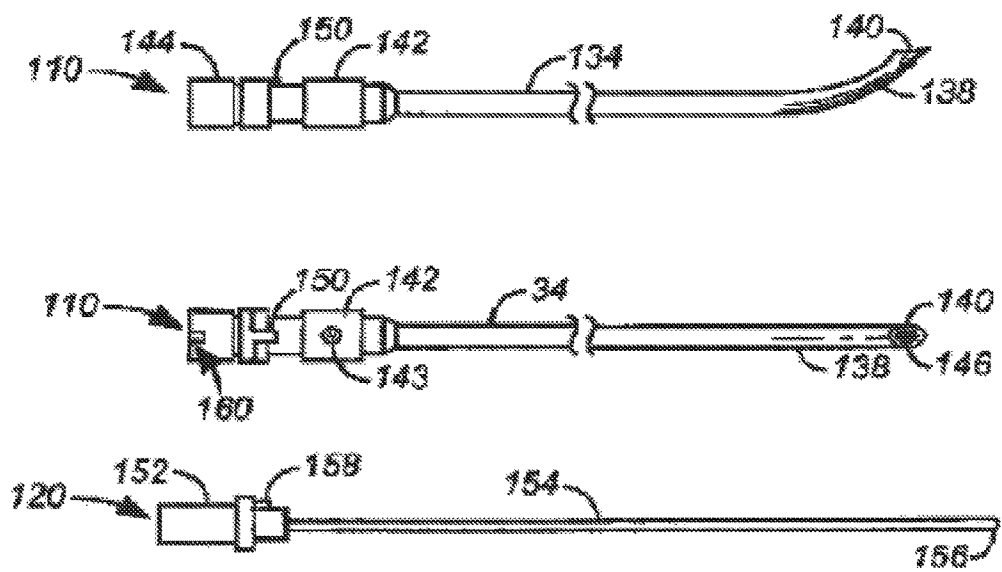

FIG. 9 is an embodiment of the present invention comprising the cannula 10 with a biopsy needle portion 226 and with a ball 220 at the distal tip 218. In this embodiment, the ball is connected to an external wire 222 which may in turn be connected to a sensor.

What is claimed is:

1. A safety neural injection system comprising:
   an at least partially hollow cannula being defined by a first inside diameter, a first outside diameter, a first length, and a distal end having an opening, wherein the at least partially hollow cannula comprises a metal ball tip at least partially covering and obstructing the opening at the distal end, wherein a maximum outer diameter of the metal ball tip abuts an inward facing wall and inner diameter of the cannula, the metal ball tip having an outward facing surface abutting the inward facing wall of the cannula at a location proximal to the distal end of the cannula;
   a wire extending along a length of the at least partially hollow cannula and directly coupled to the metal ball tip, wherein the wire is adapted to be connected to an external instrument configured to provide a signal directly to the metal ball tip via the wire;
   a side port located coaxially along the at least partially hollow cannula in fluid communication between the inside and the outside of the at least partially hollow cannula; and
   a flexible stylet with a shaped tip, wherein the flexible stylet is capable of being releasably locked in a first position within the at least partially hollow cannula and extends through the at least partially hollow cannula;
   wherein the at least partially hollow cannula proximate to the distal end includes a rigid bend so as to facilitate placement of the distal end at a target site, wherein the stylet and the at least partially hollow cannula are sized and configured to, when the stylet is positioned in the at least partially hollow cannula, enable fluid to pass between the stylet and the at least partially hollow cannula and to travel to the side port.

2. The system of claim 1, further comprising an agent selected from the group consisting of a therapeutic agent, a diagnostic agent and a prophylactic agent.

3. The system of claim 2, wherein said therapeutic agent is anesthesia.

4. The system of claim 1, further comprising a connector.

5. The system of claim 4, wherein the metal ball tip is a probe.

6. The system of claim 5, wherein the wire is adapted to be connected about the connector with the instrument.

7. The system of claim 1, further comprising insulation.

8. The system of claim 1, wherein the stylet further comprises a side port.

9. The system of claim 1, further comprising a biopsy needle.

10. A method of injecting a medicament at a neuronal tissue comprising the steps of:
   locating a target site for administration;
   adjusting the safety neural injection system of claim 1 to position the system relative to the site;
   inserting at the target site at least a portion of the safety neural injection system; and
   administering an agent about the target site.

11. The method of claim 10, wherein administering the agent about the target site comprises selecting the agent from the group consisting of a therapeutic agent, a diagnostic agent and a prophylactic agent.

12. The method of claim 11, wherein administering the agent about the target site comprises providing anesthesia.

13. The method of claim 10, further comprising creating a neural map of at least a portion of the tissue.

14. The method of claim 10, further comprising selecting the target site from the group consisting of the digestive system, the circulatory system, nervous system, muscular system, skeletal system, respiratory system, urinary system, reproductive system, excretory system, endocrine system, and the immune system of the human body.

15. A kit comprising the safety neural injection system of claim 1 and an agent to be administered.

16. The kit of claim 15, wherein said agent is selected from a group consisting of a therapeutic agent, a diagnostic agent or a prophylactic agent.

17. A safety neural injection system comprising:
   an at least partially hollow cannula being defined by an inside diameter, an outside diameter, a length, and a distal end having an opening;
   a ball defining a terminal tip of the at least partially hollow cannula, the ball having an outer diameter at least partially covering the opening at the distal end, the ball having an outward facing surface abutting an inward facing wall of the cannula at a location proximal to the distal end of the cannula;
   a side port located coaxially along the at least partially hollow cannula in fluid communication between the inside and the outside of the at least partially hollow cannula; and
   a flexible stylet with a shaped tip, wherein the flexible stylet is capable of being releasably locked in a position within the at least partially hollow cannula, wherein the at least partially hollow cannula proximate to the distal end includes a rigid bend so as to facilitate placement of the distal end at a target site, wherein the stylet and the at least partially hollow cannula are sized and configured to, when the stylet is positioned in the at least partially hollow cannula, enable fluid to pass between the stylet and the at least partially hollow cannula and to travel to the side port.

18. The system of claim 17, further comprising a wire extending along a length of the at least partially hollow cannula and coupled to the ball, wherein the wire is adapted to be connected to an external instrument configured to provide a signal to the ball via the wire.

19. A safety neural injection system comprising:
   an at least partially hollow cannula being defined by an inside diameter, an outside diameter, a length, and a distal end having an opening, wherein the at least partially hollow cannula proximate to the distal end includes a rigid bend so as to facilitate placement of the distal end at a target site;
   a ball defining a terminal tip of the at least partially hollow cannula, the ball having an outward facing surface abutting an inward facing wall of the cannula at a location proximal to the distal end of the cannula;
   a side port located coaxially along the at least partially hollow cannula, wherein only the side port is configured to provide fluid communication between the inside and the outside of the at least partially hollow cannula proximate the distal end of the at least partially hollow cannula; and
   a flexible stylet capable of being releasably locked within the at least partially hollow cannula, wherein the stylet and the at least partially hollow cannula are sized and configured to enable fluid to pass between the stylet and the at least partially hollow cannula when the stylet is positioned in the at least partially hollow cannula.

* * * * *

UNITED STATES PATENT AND TRADEMARK OFFICE
CERTIFICATE OF CORRECTION

PATENT NO. : 10,265,504 B2  
APPLICATION NO. : 14/210887  
DATED : April 23, 2019  
INVENTOR(S) : N. Sandor Racz It is certified that error appears in the above-identified patent and that said Letters Patent is hereby corrected as shown below:

In the Drawings  
Delete Drawing Sheets 1, 4, and 5 and replace with the attached Drawing Sheets 1, 4, and 5

In the Specification

| | | |
|---|---|---|
| Column 5, | Line 24, | change "Dogs", 2003," to --Dogs," 2003,-- |
| Column 5, | Line 32, | change "the term "about"." to --the term "about."-- |
| Column 19, | Line 20, | change "notch 58 shaped" to --notch 158 shaped-- |

In the Claims

| | | | |
|---|---|---|---|
| Claim 10, | Column 21, | Line 10, | change "to the site;" to --to the target site;-- |
| Claim 14, | Column 21, | Line 24, | change "of the digestive" to --of digestive-- |
| Claim 14, | Column 21, | Line 25, | change "system, the circulatory" to --system, circulatory-- |
| Claim 14, | Column 21, | Line 28, | change "the human body" to --a human body-- |

Signed and Sealed this  
Third Day of September, 2019

Andrei Iancu  
*Director of the United States Patent and Trademark Office*